United States Patent
Lee et al.

(10) Patent No.: US 11,186,609 B2
(45) Date of Patent: Nov. 30, 2021

(54) METHOD FOR PREPARING S-BZ-MAG3 AS A PRECURSOR OF CONTRAST MEDIA

(71) Applicant: INSTITUTE OF NUCLEAR ENERGY RESEARCH, ATOMIC ENERGY COUNCIL, EXE. YUAN, R.O.C., Taoyuan (TW)

(72) Inventors: Ching-Yun Lee, Taoyuan (TW); Yu Chang, Taoyuan (TW); Cheng-Fang Hsu, Taoyuan (TW)

(73) Assignee: Institute of Nuclear Energy Research, Atomic Energy Council, Executive Yuan, R.O.C., Taoyuan (TW)

( * ) Notice: Subject to any disclaimer, the term of this patent is extended or adjusted under 35 U.S.C. 154(b) by 0 days.

(21) Appl. No.: 16/157,277

(22) Filed: Oct. 11, 2018

(65) Prior Publication Data
US 2019/0106457 A1    Apr. 11, 2019

(30) Foreign Application Priority Data
Oct. 11, 2017    (TW) .................. 106134826

(51) Int. Cl.
*C07K 5/083*    (2006.01)
*C07K 1/36*    (2006.01)
*C07K 1/06*    (2006.01)

(52) U.S. Cl.
CPC ............ *C07K 5/0806* (2013.01); *C07K 1/067* (2013.01); *C07K 1/36* (2013.01)

(58) Field of Classification Search
None
See application file for complete search history.

(56) References Cited

U.S. PATENT DOCUMENTS 5,064,940 A * 11/1991 Barstow .................. C07K 1/04
530/333

FOREIGN PATENT DOCUMENTS

IN    201300740 I1 * 12/2014

OTHER PUBLICATIONS

Anonymous "Recrystallization" 1chemistry.blogspot.com/2011/08/recrystallization.html (Year: 2011).*
Grummon et al. "Synthesis, Characteriztion and Crystal Structures of Technetium(V)-Oxo Complexes Useful in Nuclear Medicine. 1. Complexes of Mercaptoacetylglycylglycylglycine (MAG3) and Its Methyl Ester Derivative (MAG3OMe)" Inorg. Chem. 34:1764-1772. (Year: 1995).*
Xiuli et al. "An improved synthesis of S-benzoyl mercaptoacetyltriglycine as BFCA and the labeling of IgG with carrier-free 188Re" J. Radioanalytical and Nuclear Chemistry 256:339-343. (Year: 2003).*
Wang J. "Rhenium complexes based on triazolyl derivatives: from synthesis, structural and theoretical characterization to application as radiopharmaceuticals or fluorophores". Disseration, Universite de Toulouse. (Year: 2017).*

* cited by examiner

*Primary Examiner* — Sudhakar Katakam
*Assistant Examiner* — Zachary J Miknis
(74) *Attorney, Agent, or Firm* — Rosenberg, Klein & Lee

(57) ABSTRACT

The present invention provides a method for preparing S-Bz-MAG3 as a precursor of contrast media. Thioglycolic acid and benzoyl chloride are taken for the thiol protection reaction. Next, N,N'-dicyclohexylcarbodiimide and N-hydroxysuccinimide are converted to corresponding ester compounds. The corresponding ester compounds then react with triglycine by amide bonding reaction. The product of the reaction is recrystallized using acetone, filtered, and finally flushed using flushing agent to give the final product. This is a bifunctional chelator and can be bridged with 99mTc and 186/188Re effectively and applied to nuclear medicine imaging and tumor radiotherapy. By taking advantage of fewer synthesis steps and ease of operations, complicated separation and purification reactions can be reduced and thus achieving highly productivity of S-Bz-MAG3.

7 Claims, 3 Drawing Sheets

| Sample number | Melting(°C) | Purity% | NMR($^1$H) | NMR($^{13}$C) | Sample status |
|---|---|---|---|---|---|
| A-722-2 | 200.97 | 99.4 | OK | OK | |
| A-724 | 201.56 | 99.5 | OK | OK | |
| A-725 | 200.47 | 99.4 | OK | OK | |
| A-723-2 | 190.5 | | | | Impurities found |
| A-723-3 | 201.4 | 99.3 | OK | OK | Solvent process 3 times; recrystallize |
| A-723-4 | 199.52 | 99.3 | OK | OK | Solvent process for 3 times |
| A-723-3 | | 99.3 | | | Solvent process 3 times; some impurities |
| A-723-6 | 197.82 | 99.4 | OK | OK | Solvent process twice |

Figure 3

METHOD FOR PREPARING S-BZ-MAG3 AS A PRECURSOR OF CONTRAST MEDIA

FIELD OF THE INVENTION

The present invention relates generally to a method for preparing precursor of contrast media, and particularly to a method for preparing S-Bz-MAG3 as a precursor of contrast media.

BACKGROUND OF THE INVENTION

The nuclear medicine, put simply, is the medicine using radiopharmaceuticals with radioactive isotopes and their labels for examining and curing patients. The examinations of the nuclear medicine can be classified into imaging examination (scan examination) and radioimmunoassay.

The general imaging examination items include whole body bone scan, myocardial perfusion scan, cerebral blood flow scan, thyroid scan, renal function scan, lung scan, liver scan, biliary tract scan, gastrointestinal bleeding scan, esophagus scan, gastric emptying scan, abscess positioning scan, and tumor scan.

The general radioimmunoassay items include, for example, hormone, hepatitis antigens or antibodies, tumor markers, prenatal examination, and Down's syndrome screening.

The so-called radiopharmaceuticals include two parts: radionuclides and their labeled compounds. Generally, the usage of the compounds with radionuclides is too few to interfere the normal biochemical reactions. Their main function is like a tracer. For examinations, the radionuclides with short half-lives and emitting γ rays are applied. On the contrary, in therapies, the radionuclides with longer half-lives and emitting γ rays are adopted.

Ideal labeled compounds should be equipped with the following properties of superior positioning capability, rapid blood flushing, rapid entrance to target organ, appropriate elimination rate from target organ, high radioactivity ratio (contrast) between target and nontarget organs, low radioactive absorptivity for human bodies, rapid elimination from nontarget organs, nontoxicity, nonthermal source, low cost, and ease of accessibility.

Radiopharmaceuticals are introduced into human bodies through injection, oral, or inhale methods and distributed to specific organs or tissues. By detecting the distribution of pharmaceuticals in specific organs or tissues using nuclear medicine instruments, the anatomical, physiological, or pathological variations of the organs or tissues can be depicted. While performing therapy, the purpose of brachytherapy can be achieved by using the biological effect of ionizing radiation of the pharmaceuticals distributed in specific organs or tissues.

Common radionuclides include technetium-99m (99mTc), iodine-131 (131I), gallium-67 (67Ga), thallium-201 (201T1), and xenon-133 (133Xe). The two radionuclides adopted most by the nuclear medicine are technetium-99m and iodine-131. Around 80% of radiopharmaceuticals are the compounds of the label technetium-99m; around 15% of radiopharmaceuticals are the label iodine-131 and the compounds of the label iodine-131; and the other radiopharmaceuticals occupy around 5% only.

In Taiwan, the prevalence of kidney disease is increasing annually. In 2012, the population of chronic kidney disease in Taiwan is 70,672. In 2015, the number is increased to 83,000, grown by 9.2% within only four years. It has become a silent new national disease and endangers compatriots' health. Unfortunately, the kidney is a silent organ. The early symptoms are not obvious. When the symptoms of darkened face, feeling like vomiting, and vomiting appear, it is usually the terminal phase of kidney disease. To avoid long-term dialysis, periodic examinations are required. Currently, there are 6,000 to 10,000 people requiring examinations each year. This proves the importance of the nuclear medicine imaging.

In recent years, technetium-99m-Mertiatide (MAG3) has been extensively applied to imaging and diagnosis for kidney functions replacing the original contrast medium iodine-131-huppurase. Compared with iodine-131, the radiation exposure of technetium-99m on an examinee is much lower. In addition, owing the differences in the physical properties between technetium-99m and iodine-131, the images of technetium-99m-MAG3 is much superior to those of iodine-131. Consequently, technetium-99m-MAG3 has replaced iodine-131 currently.

In addition, the excretion mechanism of technetium-99m-MAG3 is done through renal tubules, making it an excellent pharmaceutical for observing the urine collecting system of kidneys, evaluating obstruction of the urine system, and assessing renal tubule functions. While assessing kidney functions, because the excretion rate of technetium-99m-MAG3 is high, for some patients with bas kidney functions, high-quality images can be generated by using technetium-99m-MAG3.

Unfortunately, the original manufacturer of commercial S-Bz-MAG3 is the ABX company. The product name is S-Benzoyl-MAG-3 (product code: 7100) and the price is 258,000 dollars per gram (quoted in 1996; the acceptable range of melting point is 192-205□; and the purity is 95%). The market is monopolized by a certain vendor. Thereby, the price is kept high.

Accordingly, it is required to develop a better method for preparing S-Bz-MAG3 for achieving ease of operations, high productivity, and high purity.

SUMMARY

An objective of the present invention is to provide a method for preparing S-Bz-MAG3 as a precursor of contrast media. Thioglycolic acid and benzoyl chloride are taken for the thiol protection reaction. Next, N,N'-dicyclohexylcarbodiimide (DCC) and N-hydroxysuccinimide (NHS) are converted to corresponding ester compounds. The corresponding ester compounds then react with triglycine by amide bonding reaction. The product of the reaction is recrystallized using acetone, filtered, and finally flushed using flushing agent to give the final product. By taking advantage of fewer synthesis steps and ease of operations, complicated separation and purification reactions can be reduced and thus achieving highly productivity of S-Bz-MAG3.

Another objective of the present invention is to provide a method for preparing S-Bz-MAG3 as a precursor of contrast media. The method adopts ethyl acetate or acetone to flush and filter for eliminating the byproduct dicyclohexylurea (DCU). Thereby, high-purity S-Bz-MAG3 can be produced without lowering productivity significantly.

To achieve the above objectives, the present invention discloses a method for preparing S-Bz-MAG3 as a precursor of contrast media, comprising steps of: taking thioglycolic acid and benzoyl chloride for performing a thiol protection reaction and producing a first product; taking N,N'-dicyclohexylcarbodiimide and N-hydroxysuccinimide to react with the first product for converting to a second product; taking the second product and triglycine to perform an amide bonding reaction and producing a reaction product; using acetone to recrystallize the reaction product for forming a crystal product; filtering the crystal product; and using a flushing agent having an alkyl structure to flush the crystal product and producing a final product.

According to an embodiment of the present invention, after the step of performing the thiol protection reaction, the method further comprises steps of filtering the first product and flushing the first product using water; and drying the first product for increasing the productivity of the first product.

According to an embodiment of the method for preparing S-Bz-MAG3 as a precursor of contrast media according to the present invention, the first product is S-benzoylsulfanylacetic acid.

According to an embodiment of the present invention, the first product and the N,N'-dicyclohexylcarbodiimide are carboxylated first to form an unstable highly active complex.

According to an embodiment of the present invention, nucleophilic substitution of the highly active complex by the N-hydroxysuccinimide is performed to produce the second product.

According to an embodiment of the method for preparing S-Bz-MAG3 as a precursor of contrast media according to the present invention, the second product is an ester compound corresponding to the S-benzoylsulfanylacetic acid.

According to an embodiment of the method for preparing S-Bz-MAG3 as a precursor of contrast media according to the present invention, the second product further includes a byproduct dicyclohexylurea.

According to an embodiment of the present invention, before the step of performing the amide bonding reaction, the method further comprises a step of flushing and filtering the second product using a solvent having a methyl structure for eliminating the dicyclohexylurea.

According to an embodiment of the method for preparing S-Bz-MAG3 as a precursor of contrast media according to the present invention, the solvent further includes ethyl acetate and acetone.

According to an embodiment of the method for preparing S-Bz-MAG3 as a precursor of contrast media according to the present invention, the reaction product and the final product have different crystalline shapes.

According to an embodiment of the method for preparing S-Bz-MAG3 as a precursor of contrast media according to the present invention, the flushing agent is dichloromethane.

BRIEF DESCRIPTION OF THE DRAWINGS

FIG. 3 shows a comparison table for preparing S-Bz-MAG3 according to the present invention.

DETAILED DESCRIPTION

In order to make the structure and characteristics as well as the effectiveness of the present invention to be further understood and recognized, the detailed description of the present invention is provided as follows along with embodiments and accompanying figures.

Given that the demands in domestic nuclear medicine imaging is increasing, the present invention provides a method for preparing S-Bz-MAG3 as a precursor of contrast media to solve the problems.

In the following, the properties, the accompanying structures, and the method provided by the method for preparing S-Bz-MAG3 as a precursor of contrast media according to the present invention will be described.

Figure 1:
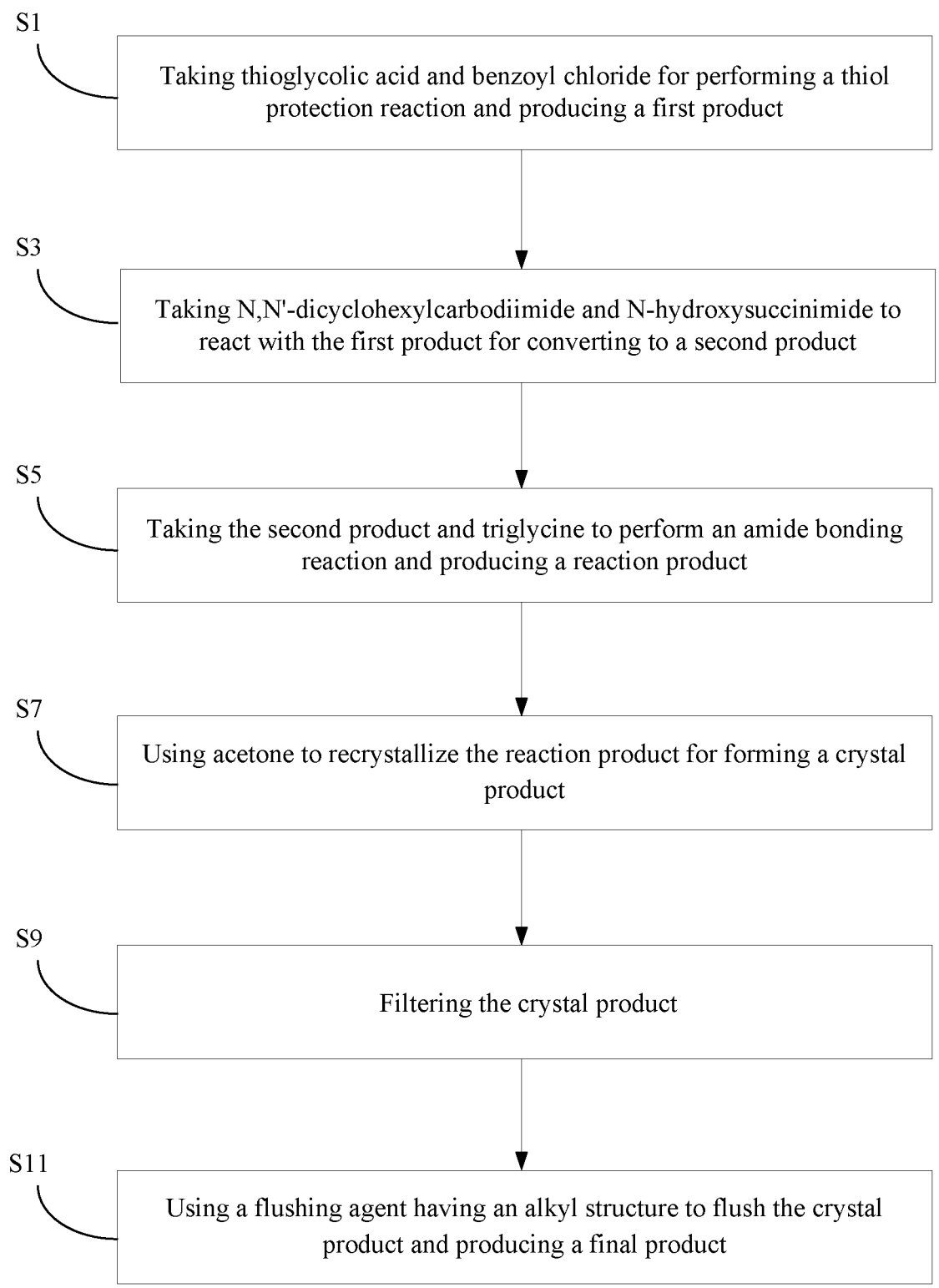
FIG. 1 shows a flowchart of the method for preparing according to the present invention.
Figure 2:
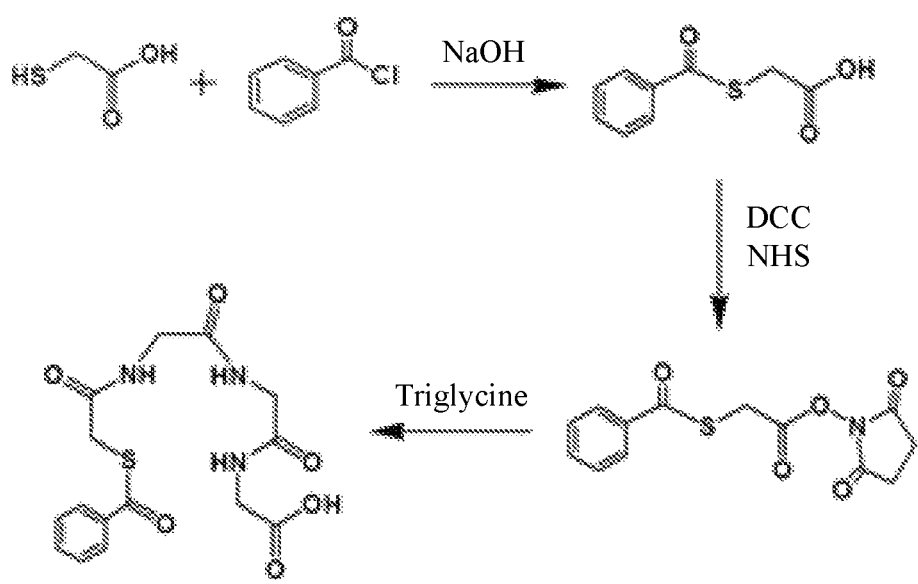
FIG. 2 shows a path diagram for preparing S-Bz-MAG3 according to the present invention.

Please refer to FIG. 1 and FIG. 2, which show a flowchart of the method for preparing and a path diagram for preparing S-Bz-MAG3 according to the present invention. As shown in the figures, the method for preparing S-Bz-MAG3 as a precursor of contrast media according to the present invention comprises steps of:

S1: Taking thioglycolic acid and benzoyl chloride for performing a thiol protection reaction and producing a first product;

S3: Taking N,N'-dicyclohexylcarbodiimide and N-hydroxysuccinimide to react with the first product for converting to a second product;

S5: Taking the second product and triglycine to perform an amide bonding reaction and producing a reaction product;

S7: Using acetone to recrystallize the reaction product for forming a crystal product;

S9: Filtering the crystal product; and

S11: Using a flushing agent having an alkyl structure to flush the crystal product and producing a final product.

As shown in the step S1, while adding the benzoyl chloride to the thioglycolic acid, the speed must be quite slow. The rate of adjusting the pH value should not be too fast. Otherwise, the productivity will be influenced.

Thereby, as shown in the step S1, when the reaction time is longer, such as the time required for recovering to the room temperature and the time of adding the benzoyl chloride and stirring slowly (extending from 30 minutes to 2 hours), the productivity of a first product can be increased from 83% to 92%.

In addition, as shown in the step S1, after the step of performing the thiol protection reaction, the method further comprises steps of filtering the first product and flushing the first product using water; and drying the first product for increasing the productivity of the first product.

The first product produced in the step S1 is S-benzoylsulfanylacetic acid. As shown in the step S3, the first product and the N,N'-dicyclohexylcarbodiimide are carboxylated first to form an unstable highly active complex.

Next, in the step S3, nucleophilic substitution of the highly active complex by the N-hydroxysuccinimide is performed to produce a second product.

The second product produced in the step S3 is an ester compound corresponding to the S-benzoylsulfanylacetic acid.

Besides, as shown in the step S3, the second product further includes a byproduct dicyclohexylurea.

The dicyclohexylurea produced in the above step S3 is not solvable in organic solvents. Although the filtering method can be adopted for elimination, minor dicyclohexylurea still might be residual in the solution. Once elimination is not complete before the next experiment, the melting point of the S-Bz-MAG3 will be influence and hence influencing the productivity.

Accordingly, as shown in the step S5, before the step of performing the amide bonding reaction, the method further comprises a step of flushing and filtering the second product using a solvent having a methyl structure for eliminating the dicyclohexylurea of the second product.

In addition, as the above step S5, the solvent further includes ethyl acetate and acetone. Moreover, the flushing and filtering should be repeated for two more times for eliminating the dicyclohexylurea completely.

As shown in the steps S5, S7, S9, S11, a reaction product produced in the step S5 and the final product, which is produced by recrystallizing by acetone in the step S7, filtering in the step S9, and flushing using a flushing agent having an alkyl structure in the step S11, have different crystalline shapes.

As shown in the step S11, the flushing agent is dichloromethane.

Compared with the total productivity of the prior art (24~52%), the total productivity using the method for preparing S-Bz-MAG3 as a precursor of contrast media according to the present invention (64%) is higher with the purity greater than or equal to 98%.

In the following, an experimental flow according to a preferred embodiment of the present invention will be described.

The method for preparing the first product according to a preferred embodiment of the present invention is to solve thioglycolate (4.6 g, 0.10 mol) in 37.5 mL methylbenzene solution and sodium hydroxide (4.4 g, 0.22 mol) in 37.5 mL deionized water. The both are mixed in an ice bath and the temperature is maintained at around 10☐. The reaction bottle is equipped with an isobaric tube and the benzoyl chloride (7.0 g, 0.10 mol) is added drop by drop. Stir for 30 minutes at 10☐. Then continue to stir for 2 hours at the room temperature (28☐). After the reaction is finished, the solution is placed in a separatory funnel. Take the lower layer (the water layer), and flush the organic layer using deionized water for four times. Next, adjust the pH value of the whole liquid-phase aqueous solution to 1 using concentrated hydrochloric acid. Filter to keep the white solid matter. Flush the solid matter using iced water and dry it to produce the white solid product (8.9 g, 92%).

The data analysis for the first product according to the present invention is:

IR (KBr): 1708 $cm^{-1}$ (—COOH), 1665 (—S—C=O) $cm^{-1}$.

1H NMR (CDCl3, 300 MHz): δ 7.99-7.95 (dd, 2H), 7.62-7.57 (t, 1H), 7.49-7.44 (t, 2H), 3.92 (s, 2H).

13C NMR (CDCl3, 75 MHz): 190.73, 175.33, 136.57, 134.67, 129.45, 128.16, 31.81.

ESI-MS: m/z 197.01 (M+H)+.

The method for preparing the second product according to a preferred embodiment of the present invention is to solve the first product (2 g, 0.0102 mmole) and NHS (1.17 g, 0.01017 mol) in 12.5 mL anhydrous tetrahydrofuran (THF) and lower the temperature to 0° C. Solve DCC (2.52 g) in 8.5 mL anhydrous THF and add the solution to the above solution using an isobaric tube. Afterwards, the for 2 hours at 0° C. Then recover to the room temperature and react overnight. Filter the reaction solution and flush twice using hot THF. Then dry the filtered solution. After recrystallizing using ethyl acetate, the white solid product (2.6 g, 86%) will be produced.

The data analysis for the second product according to the present invention is:

IR (KBr): 1820 $cm^{-1}$, 1780 $cm^{-1}$ and 1750 (ester) $cm^{-1}$, 1680 (—S—C=O) $cm^{-1}$, 1630 (—N—C=O) $cm^{-1}$.

1H NMR (CDCl3, 300 MHz): δ 8.00-7.96 (dd, 2H), 7.64-7.47 (t, 1H), 7.47-7.44 (t, 2H), 4.17 (s, 2H), 2.83 (s, 4H).

13C NMR (CDCl3, 75 MHz): 189.28, 169.29, 165.42, 136.25, 134.81, 129.49, 128.24, 28.91, 26.22.

The method for preparing the final product according to a preferred embodiment of the present invention is to mix the second product (1.35 g, 4.6 mmol) in 7 mL acetonitrile and heat it to around 60° C. for solving it. In addition, solve triglycine (870.82 mg, 4.6 mmol) in 1 N sodium hydroxide (4.5 mL). The solution is added to the previous solution and stir for 1 hour at 60° C. Then cool down to the room temperature and react for 5 hours. Filter out the insoluble matter and flush using water. Next, add concentrated hydrochloric acid (0.55 mL) to the filtered solution. The acidized solution is moved to a refrigerator (around 4° C.) for 4 hours. Filter the sediment, flush using cold water, and dry it. The coarse product is suspended in water and heated to 65° C. Besides, hot acetone is added to help solving. By cooling slowly, crystals are produced. After filtering the crystals and flushing using dichloromethane, the pure final product (1.38 g, 82%) will be produced.

The data analysis for the final product according to the present invention is:

IR (KBr): 3290 (—NH), 1708 (—COOH), 1665 (—S—C=O), 1649 (—N—C=O).

1H NMR (DMSO-d6, 300 MHz) 12.5 (s, COOH), 8.48-8.44 (t, 1H), 8.20-8.12 (q, 2H), 7.96-7.92 (dd, 2H), 7.71-7.67 (t, 1H), 7.56-7.54 (t, 2H), 3.88 (s, 2H), 3.74-3.77 (m, 6H).

13C NMR (DMSO-d6, 75 MHz): 190.30, 171.02, 169.04, 168.82, 167.17, 135.92, 134.05, 129.13, 126.86, 42.46, 42.71, 32.42.

ESI-MS: m/z 368.12 (M+H)+, 390.11 (M+Na)+.

DSC: melting point 200.97° C.

HPLC: Purity 99.5% (Elution A: 1% Acetic acid, Elution B: Methanol, Elution A/Elution B=1/9 (v/v); Column: Chromolith Performance RP-18e (4.6 mm*100 mm); Detection: UV 254 nm; flow rate: 0.3 mL/min, RT=10.4 min).

Please refer to FIG. 3, which shows a comparison table for preparing S-Bz-MAG3 according to the present invention. The examination specifications for raw material of the radiopharmaceutical MAG3 Betiatide (final product) must comply with the following four standards: 1. White power, slightly soluble in water, soluble in dimethyl sulfoxide (DMSO); 2. The range of melting point; 3. Purity lower than 98%; and 4. The NMR diagram compliance.

According to documents, the melting point of S-Bz-MAG3 is 195~197☐. According to the website of the ABX, the range of melting point of the commercial S-Bz-MAG3 (Product code: 7100) is 192~205☐. The most possible impurity in the present synthesis method is the byproduct DCU produced while synthesizing the second product. DCU is not soluble in organic solvents. Although it be can eliminated by filtering, minor residues can still exist in the solution. It is inferred that the solution is not processed clean. The cleaner the sample is processed, the high the melting point will be.

As shown in FIG. 3, the residual DCU indeed will influence the melting point. It is recommended to flush using ethyl acetate or acetone and filter twice before it is completely clean.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. A method for preparing S-Bz-MAG3 as a precursor of contrast media, comprising steps of:

taking thioglycolic acid and benzoyl chloride and stirring for 2 hours at room temperature for performing a thiol protection reaction and producing a first product;

using concentrated hydrochloric acid to adjust pH value of said first product until pH=1, then filtering said first product;

flushing said first product using water and drying said first product;

taking N,N'-dicyclohexylcarbodiimide and N-hydroxysuccinimide to react with said first product for converting to a second product, wherein said second product includes a byproduct dicyclohexylurea;

flushing and filtering said second product using ethyl acetate for eliminating said dicyclohexylurea;

taking said second product and triglycine to perform an amide bonding reaction and producing a reaction product;

using acetone to recrystallize said reaction product for forming a crystal product;

filtering said crystal product; and using a flushing agent having an alkyl structure to flush the crystal product and producing a final product.

2. The method for preparing S-Bz-MAG3 as a precursor of contrast media of claim 1, wherein said first product is S-benzoylsulfanylacetic acid.

3. The method for preparing S-Bz-MAG3 as a precursor of contrast media of claim 1, wherein said first product and said N,N'-dicyclohexylcarbodiimide are carboxylated first to form an unstable complex.

4. The method for preparing S-Bz-MAG3 as a precursor of contrast media of claim 3, wherein nucleophilic substitution of said complex by said N-hydroxysuccinimide is performed to produce said second product.

5. The method for preparing S-Bz-MAG3 as a precursor of contrast media of claim 1, wherein said second product is an ester compound corresponding to said S-benzoylsulfanylacetic acid.

6. The method for preparing S-Bz-MAG3 as a precursor of contrast media of claim 1, wherein said reaction product and said final product have different crystalline shapes.

7. The method for preparing S-Bz-MAG3 as a precursor of contrast media of claim 1, wherein said flushing agent utilized to flush the crystal product is dichloromethane.

* * * * *